United States Patent
Li et al.

(10) Patent No.: US 11,992,828 B2
(45) Date of Patent: May 28, 2024

(54) MOLECULAR SIEVES WITH INTERGROWN PHASES OF AEI AND CHA TOPOLOGIES AND CATALYST THEREOF

(71) Applicants: CHINA AUTOMOTIVE TECHNOLOGY AND RESEARCH CENTER CO., LTD, Tianjin (CN); CATARC AUTOMOTIVE TEST CENTER (TIANJIN) CO., LTD, Tianjin (CN)

(72) Inventors: Kaixiang Li, Tianjin (CN); Zhenguo Li, Tianjin (CN); Xiaoning Ren, Tianjin (CN); Yuankai Shao, Tianjin (CN); Jianhai Wang, Tianjin (CN); Li Zhang, Tianjin (CN); Lingfeng Jia, Tianjin (CN); Cheng Lv, Tianjin (CN)

(73) Assignees: CHINA AUTOMOTIVE TECHNOLOGY AND RESEARCH CENTER CO., LTD, Tianjin (CN); CATARC AUTOMOTIVE TEST CENTER (TIANJIN) CO., LTD, Tianjin (CN)

( * ) Notice: Subject to any disclaimer, the term of this patent is extended or adjusted under 35 U.S.C. 154(b) by 0 days.

(21) Appl. No.: 18/337,070

(22) Filed: Jun. 19, 2023

(65) Prior Publication Data
US 2023/0330650 A1 Oct. 19, 2023

Related U.S. Application Data

(63) Continuation of application No. PCT/CN2022/116134, filed on Oct. 12, 2022.

(30) Foreign Application Priority Data

Jan. 5, 2022 (CN) .......................... 202210002965.9

(51) Int. Cl.
| | |
|---|---|
| *B01J 29/00* | (2006.01) |
| *B01J 29/06* | (2006.01) |
| *B01J 29/068* | (2006.01) |
| *B01J 29/072* | (2006.01) |
| *B01J 29/076* | (2006.01) |
| *B01J 29/70* | (2006.01) |
| *B01J 29/74* | (2006.01) |
| *B01J 29/76* | (2006.01) |
| *B01J 29/78* | (2006.01) |
| *B01J 29/80* | (2006.01) |

(Continued)

(52) U.S. Cl.
CPC .............. *B01J 29/80* (2013.01); *B01J 29/005* (2013.01); *B01J 29/061* (2013.01); *B01J 29/068* (2013.01); *B01J 29/072* (2013.01); *B01J 29/076* (2013.01); *B01J 29/70* (2013.01); *B01J 29/7015* (2013.01); *B01J 29/74* (2013.01); *B01J 29/743* (2013.01); *B01J 29/763* (2013.01); *B01J 29/783* (2013.01); *B01J 29/83* (2013.01); *B01J 29/85* (2013.01); *B01J 37/0018* (2013.01); *B01J 37/0236* (2013.01); *B01J 37/033* (2013.01); *B01J 37/036* (2013.01); *B01J 37/06* (2013.01); *B01J 37/082* (2013.01); *C07C 2/84* (2013.01); *C10G 11/05* (2013.01); *B01J 2029/062* (2013.01); *B01J 2229/18* (2013.01); *B01J 2229/186* (2013.01)

(58) Field of Classification Search
CPC ........ B01J 29/80; B01J 29/005; B01J 29/763; B01J 29/83; B01J 29/85; B01J 29/783; B01J 29/068; B01J 29/072; B01J 29/076; B01J 29/70; B01J 29/7015; B01J 29/74; B01J 29/743; B01J 29/061; B01J 2029/062; B01J 2229/18; B01J 2229/186; B01J 37/0018; B01J 37/0236; B01J 37/06; B01J 37/036; B01J 37/082; C07C 2/84; C10G 11/05; Y02P 20/52; Y02P 30/20; Y02P 30/40; C01B 39/54; C01B 39/023; C01B 39/46; C01B 39/48
USPC ...... 502/60, 62, 63, 64, 66, 67, 69, 74, 214; 423/701, 702, 705, 707
See application file for complete search history.

(56) References Cited

U.S. PATENT DOCUMENTS

| | | | |
|---|---|---|---|
| 5,609,843 | A | 3/1997 | Wendelbo |
| 7,914,760 | B2 | 3/2011 | Mertens et al. |
| 2010/0028679 | A1 | 2/2010 | Mertens et al. |

FOREIGN PATENT DOCUMENTS

CN 114014337 A 2/2022

OTHER PUBLICATIONS

Machine Translation of CN 114014337 A, Feb. 8, 2022.*
Internation Search Report of PCT/CN2022/116134, dated Nov. 16, 2022.

* cited by examiner

*Primary Examiner* — Elizabeth D Wood
(74) *Attorney, Agent, or Firm* — True Shepherd LLC; Andrew C. Cheng

(57) ABSTRACT

The present disclosure provides molecular sieves with intergrown phases of AEI and CHA topologies and a catalyst thereof. A preparation method for the molecular sieves include the following steps: mixing a hydroxyphosphono organic alkali R with an aluminum source and a silicon source to obtain a sol-gel precursor, putting the sol-gel precursor into a closed hydrothermal synthesis reactor for reaction, filtering the reaction solution, washing, drying, and calcination to obtain the molecular sieves with intergrown phases of AEI and CHA topologies. The molecular sieves and the catalyst thereof can be directly synthesized under mild conditions with a hydroxyphosphono organic alkali as a structure-directing agent and a phosphorus source, have a (Continued)

pH value of 6-9 and low requirements for corrosion resistance of production devices, and are suitable for large-scale production.

5 Claims, 8 Drawing Sheets

(51) Int. Cl.
*B01J 29/83* (2006.01)
*B01J 29/85* (2006.01)
*B01J 37/00* (2006.01)
*B01J 37/02* (2006.01)
*B01J 37/03* (2006.01)
*B01J 37/06* (2006.01)
*B01J 37/08* (2006.01)
*C07C 2/84* (2006.01)
*C10G 11/05* (2006.01)

MOLECULAR SIEVES WITH INTERGROWN PHASES OF AEI AND CHA TOPOLOGIES AND CATALYST THEREOF

CROSS-REFERENCE TO RELATED APPLICATIONS

This application is a continuation of International Patent Application No. PCT/CN2022/116134 with a filing date of Aug. 31, 2022, designating the United States, and further claims priority to Chinese Patent Application No. 202210002965.9 with a filing date of Jan. 5, 2022. The content of the aforementioned applications, including any intervening amendments thereto, are incorporated herein by reference.

TECHNICAL FIELD

The present disclosure belongs to the field of catalysts, in particular to molecular sieves with intergrown phases of AEI and CHA topologies and a catalyst thereof.

DESCRIPTION OF RELATED ART

The production and sales of internal combustion engines in China have ranked first in the world for more than consecutive ten years. In 2020, the national sales of internal combustion engines reached 46.813 million units, in which the sales of diesel internal combustion engines were 6.341 million units, accounting for 13.5% of the total sales of internal combustion engines, and showing a steady growth tendency. From the perspective of application fields, in 2020, the sales of diesel internal combustion engines in commercial vehicles were 3.2872 million units, 926,500 units in construction machinery, and 1.6552 million units in agricultural machinery. The accompanying issue of exhaust emissions has become increasingly prominent, posing a serious threat to the sustainable development of the atmospheric and ecological environment. Since 2013, China has continuously increased its efforts to prevent and control diesel vehicle pollution, upgraded relevant emission standards, and lowered emission limits. The emission standards for diesel vehicles in China mainly follow the European emission regulations. Selective catalytic reduction (SCR) technology is one of the key after-treatment systems for diesel vehicles to meet VI emission standards and regulations. Core catalysts required by $NH_3$-SCR (ammonia selective catalytic reduction) technology which is an internationally recognized efficient technology purifying $NO_X$ by catalyzing, have been transformed from conventional vanadium-tungsten-titanium systems to molecular sieve-based catalysts. Such catalysts are composed of molecular sieves as carriers to support active metals. Common molecular sieve framework types include MFI, AEI, BEA, LTA, CHA, AFX, etc., and common active ingredients include Cu, Fe, Ce, Mn, etc.

In recent years, with the deepening of research, it has been found that multi-dimensional porous and intergrown molecular sieves have better low-temperature performance, durability, and temperature windows. Among them, molecular sieves with intergrown phases of AEI and CHA topologies are representative. According to the Patent CN101208149A, silicoaluminophosphate molecular sieves including at least one of AEI and CHA symbiotic topologies are disclosed: $(n)SiO_2/Al_2O_3/(m)P_2O_5/(x)R/(y)H_2O$, where n is a value in a range of about 0.005 to about 0.6, m is a value in a range of about 0.6 to about 1.2, x is a value in a range of about 0.5 to about 0.99, and y is a value in a range of about 10 to about 40; according to the Patent CN105174286A, molecular sieves with high-proportion of intergrown phases of AEI/CHA (SAPO-18/SAPO-34) topologies and a preparation method therefor, where N, N-diisopropylethylamine and triethylamine are used as dual templates to synthesize intergrown molecular sieves with a high proportion of AEI (SAPO-18) topology; according to the Patents CN111115655A, CN112619697A, and CN112209406A, preparation methods for a molecular sieve with intergrown phases of AEI and CHA topologies using dual templates, composite molecular sieves and use thereof in methanol-to-olefin technology are disclosed; according to the Patents CN109794286A and CN112495426B, composite denitrification catalysts with intergrown phases of CHA and AEI topologies are disclosed, carriers of which are formed by complexing SSZ-13 molecular sieves and SSZ-39 molecular sieves; according to the Patent CN113070097A, copper-based catalysts for ammonia selective catalytic reduction of $NO_X$ and a preparation method therefor are disclosed, where a preferred catalyst is Cu-CHA and Cu-AEI catalysts; according to the Patent CN112969662A, a method for preparing molecular sieves with intergrown phases of CHA and AEI topologies based on dual templates is disclosed; and according to the Patent CN110422856A, a method for preparing silicoaluminum-type catalysts containing molecular sieves with intergrown phases of CHA and AEI topologies and use thereof in SCR catalysis are disclosed, where the carrier is non-silicoaluminophosphate (SAPO) molecular sieves.

Dual templates are used in the most of foregoing patents to direct the generation of CHA and an AEI topologies, respectively. The method generally suffers from uneven growth, irregular structure, and poor product consistency of molecular sieves with two crystal phases, because the two templates cannot be evenly distributed in an aqueous phase. Uneven local distribution will seriously affect the quality of the molecular sieves and catalysts thereof. Meanwhile, there are still problems in the synthesis process of molecular sieves in the prior art, such as harsh synthesis conditions, difficult treatment of waste liquid, and complex processes. In the preparation process of molecular sieve catalysts, there are problems of low ion exchange efficiency of active ingredients, long cycle of step-by-step catalyst preparation, and the like.

SUMMARY OF PRESENT INVENTION

In view of this, the present disclosure aims to provide molecular sieves with intergrown phases of AEI and CHA topologies and a catalyst thereof, to simplify a preparation process for molecular sieves, improve distribution evenness of active ingredients in the synthesis process of molecular sieve catalysts, and increase activity and durability of catalysts.

In order to achieve the above objectives, the technical solution of the present disclosure is implemented as follows:

Molecular sieve with intergrown phases of AEI and CHA topologies are provided. Based on a formation mechanism of molecular sieves with intergrown topologies and chemical characteristics of structure-directing agents, a hydroxyphosphono organic alkali compound is directly used as a structure-directing agent for intergrown phases of AEI and CHA topologies, and is also used as a phosphorus source in synthesis raw materials for the molecular sieves, thereby accurately controlling phosphorus content and avoiding the introduction of caustic alkali. H-type molecular sieves with intergrown phases of AEI and CHA topologies can be prepared through hydrothermal synthesis. A preparation method for the molecular sieves specifically includes the following steps:

(1) dissolving a hydroxyphosphono organic alkali R in deionized water and stirring evenly; adding an aluminum source, quickly stirring and dispersing the mixture to be gelatinous, slowly adding a silicon source, stirring and reacting for 2 h-6 h, then standing for fully aging to obtain a sol-gel precursor, where the aluminum source and the silicon source are calculated based on $Al_2O_3$ and $SiO_2$ respectively, a mass ratio of the silicon source, the aluminum source, the hydroxyphosphono organic alkali R, and the deionized water is $SiO_2$:$Al_2O_3$:R:$H_2O$=(0.01-30):1:(0.2-30):(5-300), and depending on acidity and alkalinity of raw materials, a pH value of the sol-gel precursor is in a range of 6-9; and (2) putting the sol-gel precursor into a closed hydrothermal synthesis reactor for isothermal hydrothermal reaction at 130° C.-220° C. for 6.5 h-48 h, followed by pressure relief, solid-liquid separation, thorough washing of a filter cake, drying, and calcination, to obtain H-type molecular sieves with intergrown phases of AEI and CHA topologies.

The aluminum source used in Step (1) may be an aluminum sol. When the aluminum sol is added dropwise with stirring, the addition is suspended after 75%-80% of that is added, the stirring rate is increased for 10 min-30 min until a well-mixed sol-gel is formed, and the previous process is repeated for 2 to 3 times until the remaining aluminum sol is added. With the addition of the aluminum sol, the viscosity of the solution slowly increases. Increasing the stirring rate may destroy the coagulation of aluminum sol and mix the aluminum sol uniformly to form a well-mixed sol-gel;

n Step (1), the operation of standing for fully aging aims to achieve full self-assembly of O—Al—O and O—Si—O bonds in the silicon sol and the aluminum sol under the directing of the structure-directing agent, whereby a framework type of the precursor for molecular sieves with intergrown phases of AEI and CHA topologies is better formed, and the prepared molecular sieves have a more uniform particle size, a more regular structure, and a higher crystallinity; and The sol-gel precursor in Step (2) forms cuboid sheet-like molecular sieves with intergrown phases of AEI and CHA topologies having regular morphology after nucleation, growth, and maturation, and the molecular sieves with intergrown phases of AEI and CHA topologies have an alkali metal content of less than 500 ppm.

Further, the molecular sieves include at least one of $AlPO_4$-18, SAPO-18, and SSZ-39 with the AEI topology and at least one of SSZ-13, SAPO-34, SAPO-44, ZK-14, and $AlPO$-34 with the CHA topology, and the both are effectively complexed to form a periodic framework topology, rather than a simple mixture of the two topologies of molecular sieves.

Further, main characteristic diffraction peaks 2θ of the molecular sieves with intergrown phases of AEI and CHA topologies in X-ray (in particular to K α-ray) Diffraction Pattern are 9.76°±0.1°, 13.21°±0.1°, 16.43°±0.1°, 17.52°±0.1°, 18.19°±0.1°, 19.53°±0.1°, 21.03°±0.1°, 21.76°±0.1°, 21.89°±0.1°, 24.45°±0.1°, 25.36°±0.1°, 25.47°±0.1°, 26.43°±0.1°, 26.56°±0.1°, 26.58°±0.1°, 28.24°±0.1°, 28.77°±0.1°, 28.97°±0.1°, 30.66°±0.1°, 31.11°±0.1°, 31.28°±0.1°, 31.62°±0.1°, 31.76°±0.1°, 32.86°±0.1°, 35.21°±0.1°, and 49.82°±0.1°.

Further, the hydroxyphosphono organic alkali R has a molecular weight of less than 5,000, and contains at least one of cations shown in Formulas I-XI:

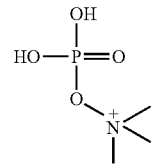

Formula I

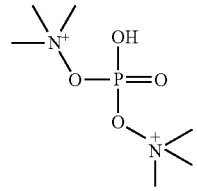

Formula II

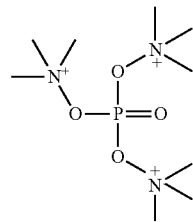

Formula III

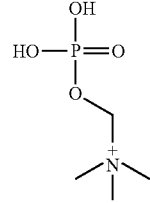

Formula IV

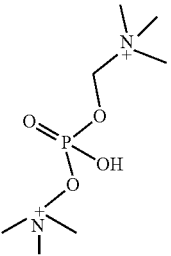

Formula V

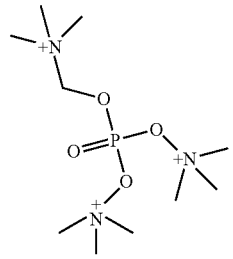

Formula VI

Formula VII
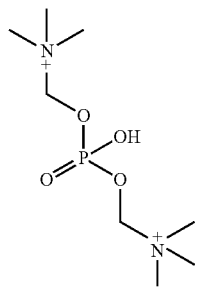

Formula VIII
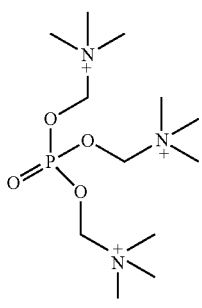

Formula IX
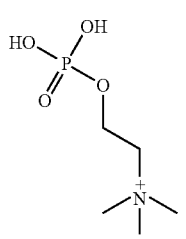

Formula X
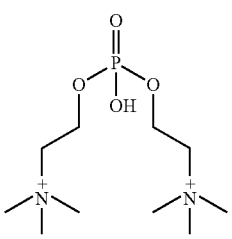

Formula XI
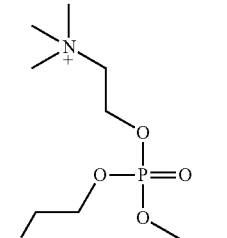

Formula XII
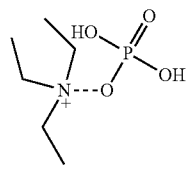

Formula XIII
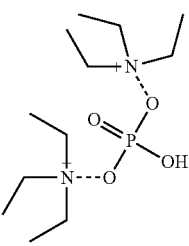

Formula XIV
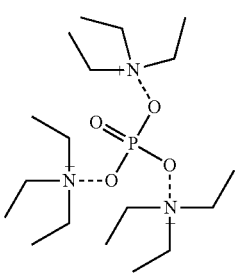

Formula XV
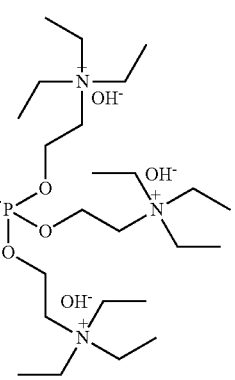

Formula XVI
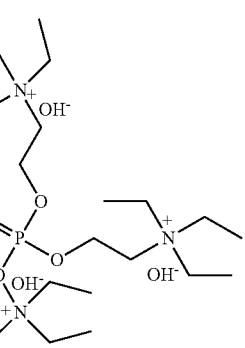

Further, an anion of the hydroxyphosphono organic alkali R is at least one selected from a group consisting of $OH^-$, $Cl^-$, $NO_3^-$, $F^-$, $Br^-$, $HCO_3^-$, $CO_3^{2-}$, $HSO_3^-$, and $HSO_4^-$.

Further, a molecule of the hydroxyphosphono organic alkali R has a size of less than 3.7 angstroms in an aqueous phase; and preferably, the hydroxyphosphono organic alkali R includes at least one of compounds shown in Formulas XII-XIX:

-continued

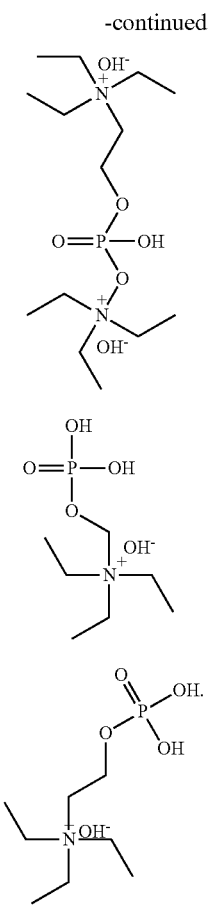

Formula XVII

Formula XVIII

Formula XIX

Molecular sieve-based catalysts with intergrown phases of AEI and CHA topologies include the foregoing molecular sieves with intergrown phases of AEI and CHA topologies and an active metal element M.

Further, a preparation method for the molecular sieve-based catalysts with intergrown phases of AEI and CHA topologies include the following steps:

adding a hydroxyphosphono organic alkali R into deionized water and thoroughly stirring to dissolve; adding a precursor of an active metal element M, and performing a complexing reaction for 0.5 h-6 h; then adding an aluminum source dropwise, suspending the addition when 75% of the aluminum source is added, and increasing the stirring rate for 10 min-30 min until a well-mixed sol-gel is formed; further, adding the remaining aluminum source dropwise and repeating for 2-3 times; slowly adding a silicon source dropwise under violent stirring and then continuing the stirring to react for 2 h-6 h; subsequently, standing for fully aging; and then transferring to a closed hydrothermal synthesis reactor, and performing an isothermal hydrothermal reaction at a temperature selected from a range of 130° C.-220° C. for 6.5 h-48 h, followed by pressure relief, solid-liquid separation, thorough washing of a filter cake, drying, and calcination, to obtain molecular sieve-based catalysts with intergrown phases of AEI and CHA topologies, where the aluminum source, the silicon source, and the precursor of M are calculated based on $Al_2O_3$, $SiO_2$, and M respectively, and a mass ratio of the silicon source, the aluminum source, the hydroxyphosphono organic alkali R, the deionized water, and the precursor of M is $SiO_2:Al_2O_3:R:H_2O:M=(0.01-30):1:(0.2-30):(5-300):(0.005-5)$.

Further, the active metal element M is at least one selected from a group consisting of Cu, Fe, Co, Mo, Mn, Sm, Pd, Pt, Rh, Au, Ag, Ru, Ni, Nb, and Cr.

Further, an coordination anion in the precursor of M is at least one selected from a group consisting of $OH^-$, $Cl^-$, $NO_3^-$, $F^-$, $CN^-$, $SCN^-$, $HCOO^-$, $CH_3COO^-$, $HSO_3^-$, $NH_3$, and EDTA.

In the preparation process of the foregoing preparation method for the molecular sieve-based catalysts with intergrown phases of AEI and CHA topologies, the active metal element is uniformly distributed in micropores or cages of the molecular sieves during assembly of the AEI and CHA framework types, and tightly bound in ion exchange sites, which is superior to impregnation and ion exchange; The hydroxyphosphono organic alkali template R is effectively complexed with the active metal element M, and is used as a structure-directing agent for the molecular sieves with intergrown phases of AEI and CHA topologies; According to the preparation method for the molecular sieve-based catalysts with intergrown phases of AEI and CHA topologies, a mass percentage of the active metal element M in the molecular sieve-based catalysts with intergrown phases of AEI and CHA topologies after drying and calcination is in a range of 0.01%-25%, and preferably 1.5%-6.5%; and Further, the active metal element M is Cu, and a promoter element Mo is further included to obtain $Cu-M_0$/AEI-CHA catalysts, where Mo is at least one selected from a group consisting of Fe, Mn, Ce, Mo, La, Y, Sm, Co, Pt, Pd, Ag, Au, and Sn.

Use of the molecular sieves with intergrown phases of AEI and CHA topologies or the catalyst thereof in the fields of selective catalytic reduction, methanol to olefins, or catalytic cracking, especially in the fields of Urea Selective Catalytic Reduction (Urea-SCR) technologies for exhaust denitrification from fixed source and exhaust from mobile source.

Compared with the prior art, the molecular sieves with intergrown phases of AEI and CHA topologies and the catalyst thereof in the present disclosure have the following advantages:

(1) The molecular sieves with intergrown phases of AEI and CHA topologies and the catalyst thereof can be directly synthesized under mild conditions with hydroxyphosphono organic alkali as a structure-directing agent and a phosphorus source, have a pH value in a range of 6-9 and low requirements for corrosion resistance of production devices, and are suitable for large-scale production;

(2) No caustic alkali is introduced in the preparation process of the intergrown molecular sieves with intergrown phases of AEI and CHA topologies and the catalyst thereof, so violent heat release and viscosity increase are avoided in the synthesis process; an H-type molecular sieve product can be obtained through drying and calcination without an ammonium exchange process, and active ingredients can be directly supported to prepare the catalyst;

(3) In the preparation process of the molecular sieves with intergrown phases of AEI and CHA topologies and the catalyst thereof, a molecular sieve catalyst with quantitative active ingredients may be prepared in one step by controlling the addition, so synthesis steps and waste liquid discharge are reduced; the active ingredients are directly bound to the ion exchange sites of the molecular sieves with intergrown phases of AEI and CHA topologies under the complexing effect of the structure-directing agent and uniformly distributed in the micropores of the molecular sieves, so the activity and durability of the molecular sieves are significantly superior to those in the conventional impregnation or ion exchange method; and (4) The molecular sieves with intergrown phases of AEI and CHA topologies and the catalyst thereof are applicable to many fields such as selective catalytic reduction technology (Urea-SCR), methanol-to-olefin technology (MTO), and fluid catalytic cracking technology (FCC), where the molecular sieve-based SCR catalyst with intergrown phases of AEI and CHA topologies has a low-temperature performance $T_{50}=130°$ C., an active temperature window $T_{90}$ of 160° C.-475° C., and a nitrogen selectivity close to 100%.

BRIEF DESCRIPTION OF THE DRAWINGS

The accompanying drawings constituting a part of the present disclosure are used to provide further understanding of the present disclosure, and the illustrative examples of the present disclosure and the descriptions thereof are used to interpret the present disclosure, rather than constituting improper limitations to the present disclosure. In the figures.

DESCRIPTION OF THE EMBODIMENTS

Figure 1:
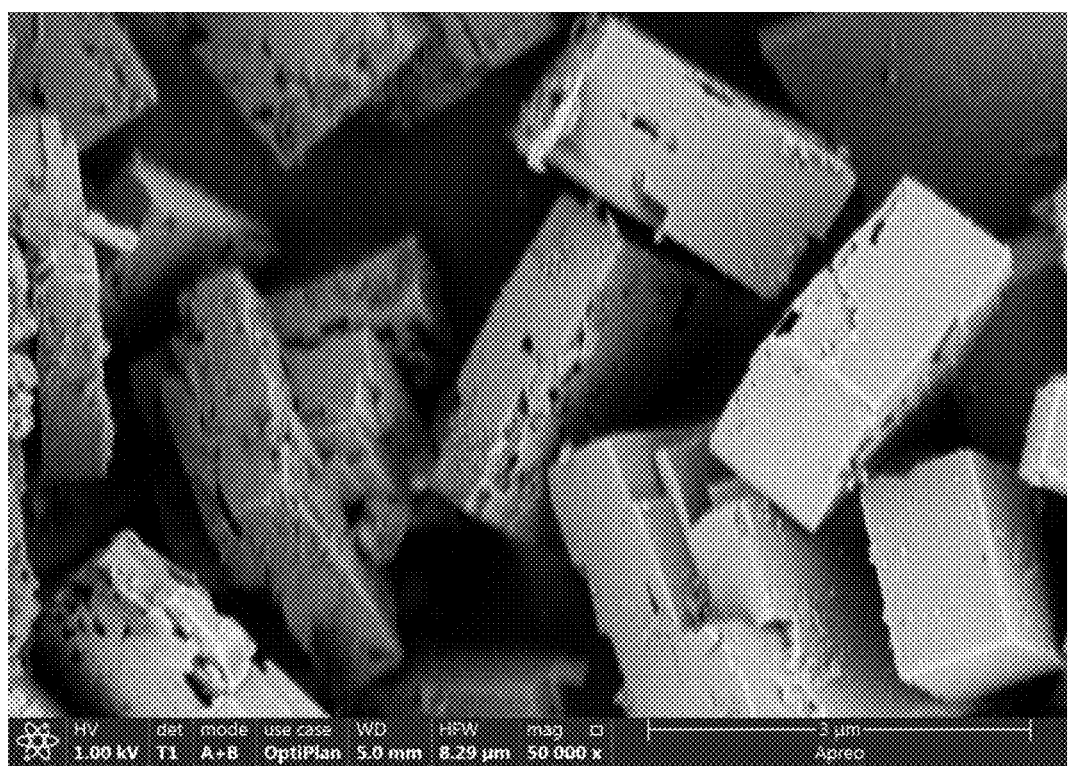
FIG. 1 is a schematic diagram showing a micro morphology of a molecular sieve product prepared in Example 1 of the present disclosure.

Unless otherwise defined, the technical terms used in the following examples have the same meanings as those commonly understood by a person skilled in the art to which the present disclosure belongs. Test reagents used in the following examples are all conventional biochemical reagents, unless otherwise specified; and the experimental methods are conventional ones, unless otherwise specified.

The present disclosure will be explained in detail below in conjunction with examples and the accompanying drawings.

Based on a formation mechanism of molecular sieves with intergrown topologies and chemical characteristics of structure-directing agents, a hydroxyphosphono organic alkali compound is directly used as a structure-directing agent for intergrown phases of AEI and CHA topologies, and is also used as a phosphorus source in synthesis raw materials for the molecular sieves, thereby solving the foregoing problems and accurately controlling phosphorus content. H-type molecular sieves with intergrown phases of AEI and CHA topologies are directly synthesized by adjusting a pH value of a synthesis system without adding caustic alkali, and may be directly used as a carrier to prepare molecular sieve-based SCR catalysts with intergrown phases of AEI and CHA topologies without an ammonium exchange process, and the molecular sieves with intergrown phases of AEI and CHA topologies and the catalyst thereof may be used in a selective catalytic reduction technology (Urea-SCR), a methanol-to-olefin technology (MTO), and a fluid catalytic cracking technology (FCC).

Example 1

A template used in this example is as shown in Formula XIII ($C_{12}H_{33}N_2O_6P$). 20 g of the template is dissolved in 150 ml of deionized water, the solution is stirred thoroughly at room temperature, 25 g of aluminum sol with a solid content of 30% is slowly added dropwise, and the solution is violently stirred for 30 min to form a milky white sol-gel; 10 g of aluminum sol is added, and the sol-gel is violently stirred for 10 min; and 5 g of the remaining aluminum sol is added, and the sol-gel is violently stirred for 3 h to obtain a milky white sol-gel. Subsequently, 30 g of silicon sol with a solid content of 30% is added, and the sol-gel is stirred to react for 2 h to obtain a sol-gel precursor for H-type molecular sieves with intergrown phases of AEI and CHA topologies.

The sol-gel precursor for H-type molecular sieves with intergrown phases of AEI and CHA topologies is stood to age for 12 h, then transferred to a hydrothermal synthesis reactor, heated to 165° C. at 4° C./min, and crystallized with stirring at a constant temperature for 24 h. After the reaction is completed, solid-liquid separation is performed by using a plate and frame filter press, a filter cake is washed repeatedly with clear water until the product is neutral, and the product is dried at 120° C. until the water content of the product is less than 6 wt %, and then calcined, and the product is heated to 350° C. at a rate of 2° C./min, preserved at a constant temperature for 1 h, then heated to 550° C., and preserved at a constant temperature for 6 h to obtain a solid product of white powder.

Figure 7:
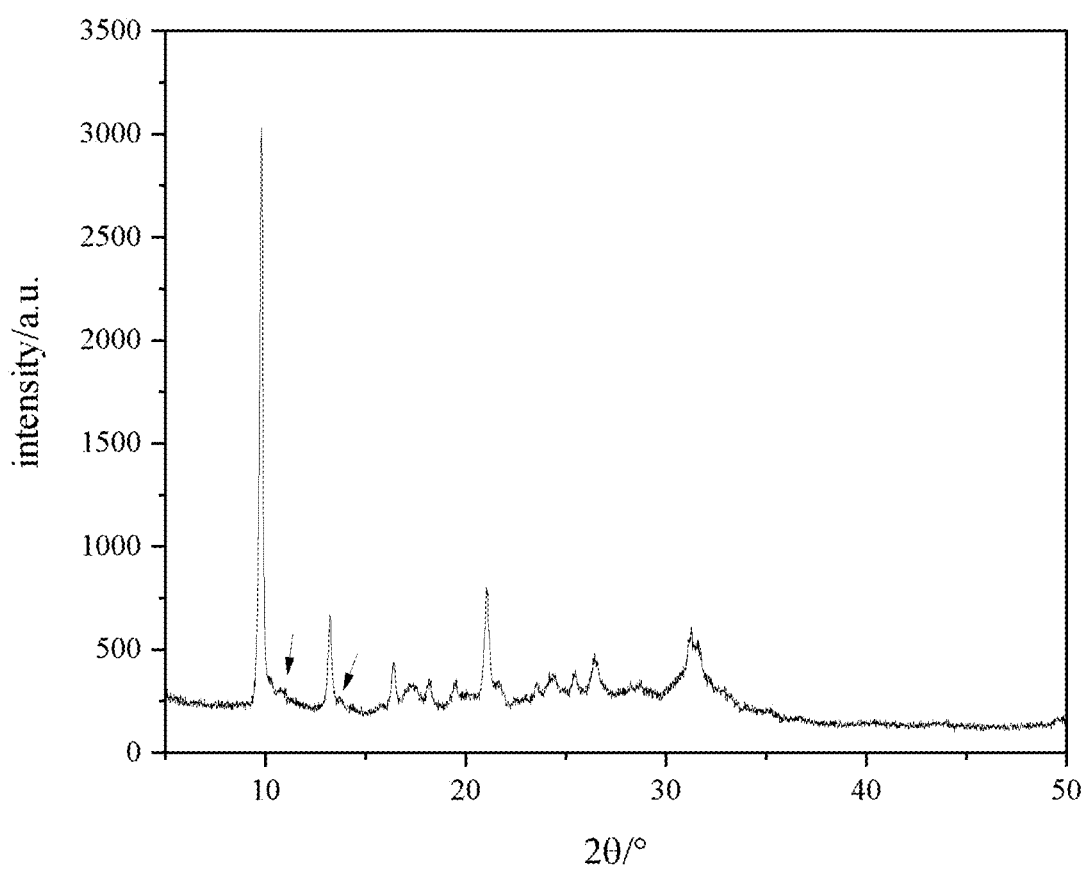
FIG. 7 is a schematic diagram showing characteristic diffraction peak pattern of a molecular sieve product prepared in Example 1 of the present disclosure.

X-Ray Diffraction (XRD) characterization results indicate that the solid product has an intergrown phase of AEI and CHA topologies, and the data about the test result are shown in FIG. 7 and Table 1; X-ray Fluorescence (XRF) characterization indicates that the content of the alkali metal (Na or K) in the product is less than 500 ppm; and Scanning Electron Microscope (SEM) characterization indicates that the product is cubic sheet-like, as shown in FIG. 1.

TABLE 1

| XRD characterization results | | | | | | | |
|---|---|---|---|---|---|---|---|
| 2-Theta | d | BG | Height | I % | Area | I % | FWHM |
| 9.761 | 9.0541 | 20 | 1,891 | 100.0 | 39,735 | 100.0 | 0.179 |
| 13.210 | 6.6966 | 11 | 333 | 17.6 | 6,788 | 17.1 | 0.173 |
| 16.428 | 5.3914 | 14 | 170 | 9.0 | 4,565 | 11.5 | 0.228 |
| 17.520 | 5.0577 | 27 | 70 | 3.7 | 1,188 | 3.0 | 0.144 |
| 18.188 | 4.8734 | 16 | 93 | 4.9 | 1,073 | 2.7 | 0.098 |
| 19.527 | 4.5423 | 18 | 106 | 5.6 | 2,358 | 5.9 | 0.189 |
| 21.030 | 4.2209 | 19 | 407 | 21.5 | 12,632 | 31.8 | 0.264 |
| 21.758 | 4.0812 | 20 | 89 | 4.7 | 1,317 | 3.3 | 0.126 |
| 21.889 | 4.0571 | 23 | 50 | 2.6 | 340 | 0.9 | 0.058 |
| 24.453 | 3.6372 | 20 | 62 | 3.3 | 450 | 1.1 | 0.062 |
| 25.362 | 3.5089 | 17 | 74 | 3.9 | 796 | 2.0 | 0.091 |
| 25.473 | 3.4939 | 17 | 84 | 4.4 | 431 | 1.1 | 0.044 |

TABLE 1-continued

XRD characterization results

| 2-Theta | d | BG | Height | I % | Area | I % | FWHM |
|---|---|---|---|---|---|---|---|
| 26.429 | 3.3696 | 14 | 122 | 6.5 | 3,970 | 10.0 | 0.277 |
| 26.562 | 3.3531 | 12 | 114 | 6.0 | 1,317 | 3.3 | 0.098 |
| 26.577 | 3.3512 | 12 | 85 | 4.5 | 1,494 | 3.8 | 0.149 |
| 28.239 | 3.1576 | 11 | 69 | 3.6 | 303 | 0.8 | 0.037 |
| 28.768 | 3.1008 | 8 | 53 | 2.8 | 604 | 1.5 | 0.097 |
| 28.971 | 3.0794 | 12 | 52 | 2.7 | 303 | 0.8 | 0.050 |
| 30.663 | 2.9133 | 12 | 88 | 4.7 | 1,371 | 3.5 | 0.132 |
| 31.110 | 2.8724 | 42 | 171 | 9.0 | 3,974 | 10.0 | 0.198 |
| 31.280 | 2.8572 | 43 | 221 | 11.7 | 7,382 | 18.6 | 0.284 |
| 31.619 | 2.8273 | 15 | 174 | 9.2 | 8,229 | 20.7 | 0.402 |
| 31.759 | 2.8152 | 13 | 136 | 7.2 | 2,590 | 6.5 | 0.162 |
| 32.855 | 2.7238 | 11 | 17 | 0.9 | 229 | 0.6 | 0.115 |
| 35.210 | 2.5468 | 5 | 51 | 2.7 | 294 | 0.7 | 0.049 |
| 49.825 | 1.8286 | 21 | 42 | 2.2 | 375 | 0.9 | 0.076 |

Example 2

Figure 2:
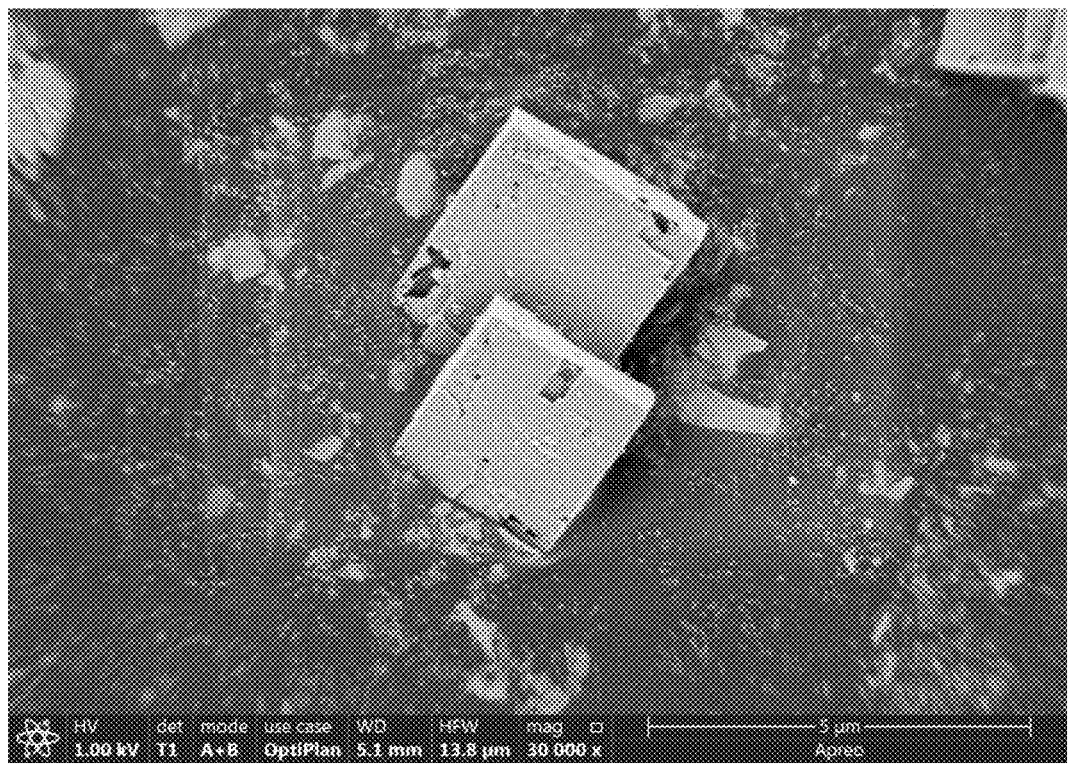
FIG. 2 is a schematic diagram showing a micro morphology of a molecular sieve product prepared in Example 2 of the present disclosure.

The preparation conditions and preparation process of this example are the same as those of Example 1, except that a template ($C_{18}H_{48}N_3O_7P$), with a chemical structure shown in Formula XIV is used. The obtained solid product is characterized by SEM, showing that the product is cubic sheet-like, as shown in FIG. 2; and XRF characterization results indicate that the content of the alkali metal (Na or K) in the product is less than 500 ppm.

Example 3

Figure 3:
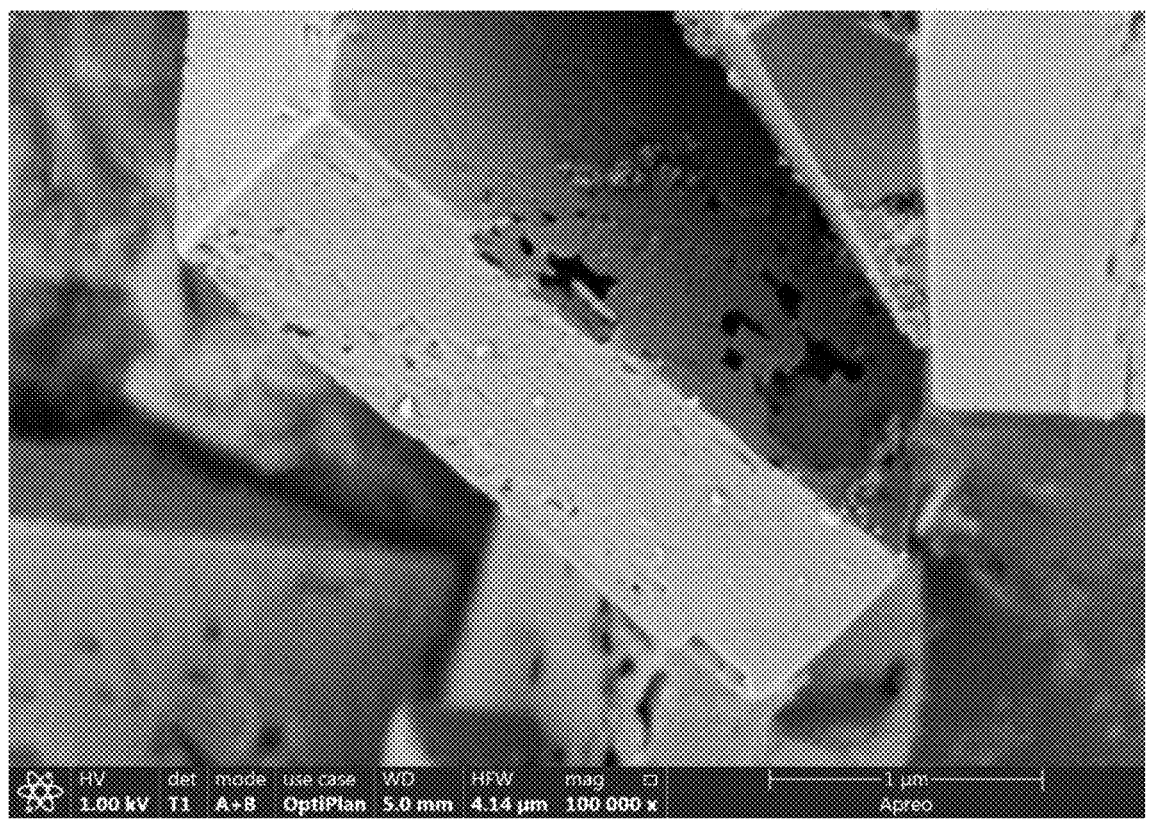
FIG. 3 is a schematic diagram showing a micro morphology of a molecular sieve product prepared in Example 3 of the present disclosure.

The preparation conditions and preparation process of this example are the same as those of Example 1, except that a template ($C_{22}H_{56}N_3O_7P$), with a chemical structure shown in Formula XV is used. FIG. 3 is an SEM photo of the obtained solid product, showing that the product is cubic sheet-like morphology; and XRF characterization results indicate that the content of the alkali metal (Na or K) in the product is less than 500 ppm.

Example 4

Figure 4:
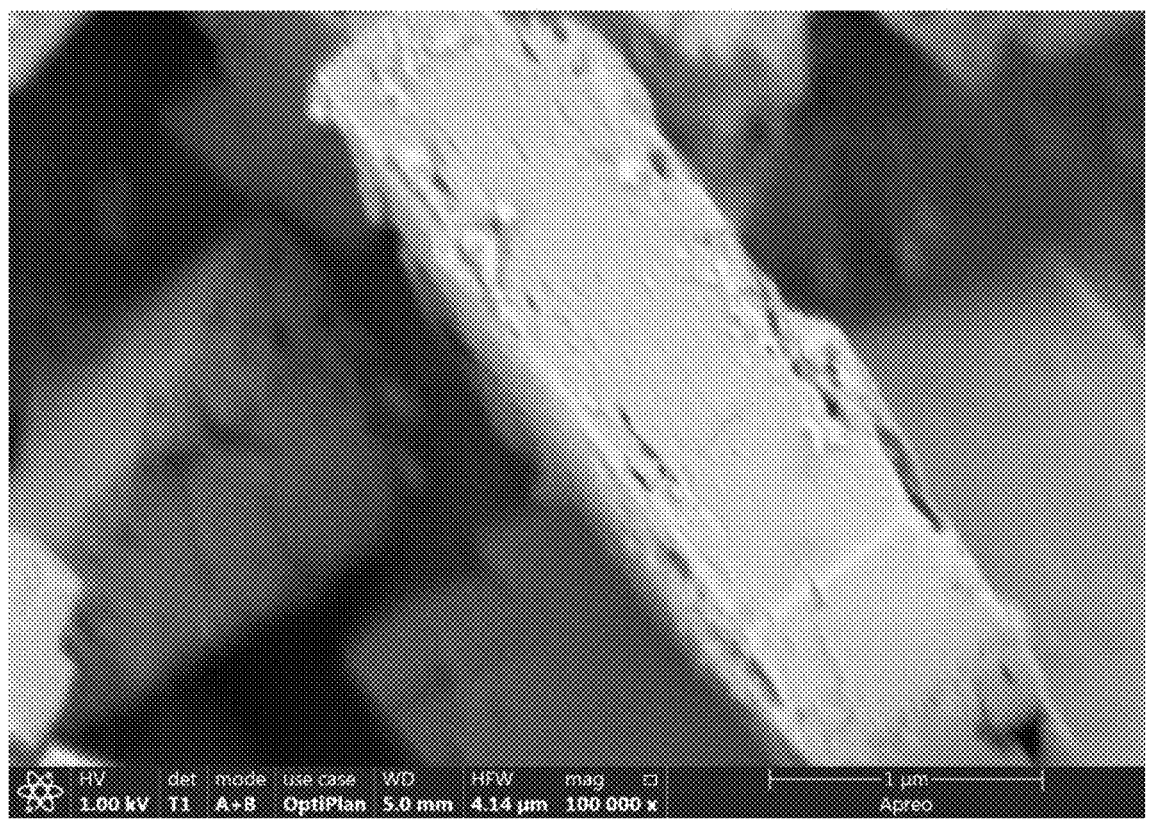
FIG. 4 is a schematic diagram showing a micro morphology of a molecular sieve product prepared in Example 4 of the present disclosure.

The preparation conditions and preparation process of this example are the same as those of Example 1, except that two templates in a molar ratio of 1:1 are used, and structural formulas of the two templates are as shown in Formula XII and Formula XIV. FIG. 4 is an SEM photo of the obtained solid product, showing that the product is cubic sheet-like; and XRF characterization results indicate that the content of the alkali metal (Na or K) in the product is less than 500 ppm.

Example 5

The addition of raw materials and the preparation process in this example are the same as those in Example 1, except that the aging time is set to 48 h, and the sol-gel is transferred to a hydrothermal synthesis reactor, heated to 170° C., and crystallized at a constant temperature with stirring for 12 h.

An SEM photo of the obtained solid product shows that the product is cubic sheet-like; and XRF characterization results indicate that the content of the alkali metal (Na or K) in the product is less than 500 ppm.

Comparative Example 1

Triethylamine is one of commonly used templates for preparing molecular sieves with intergrown phases of AEI and CHA topologies.

30 g of triethylamine is added into deionized water and dispersed by stirring. Subsequently, 44 g of phosphoric acid is slowly added, the stirring is continued for 30 min, 60 g of aluminum sol with a solid content of 25% and 40 g of silicon sol with a solid content of 30% are added, and the sol is stood to age for 12 h.

After aging, the sol-gel is transferred to a hydrothermal synthesis reactor, heated to 160° C., and stood at a constant temperature for 48 h. A solid product is obtained through filtration, washing, drying, and calcination after crystallization.

Figure 5:
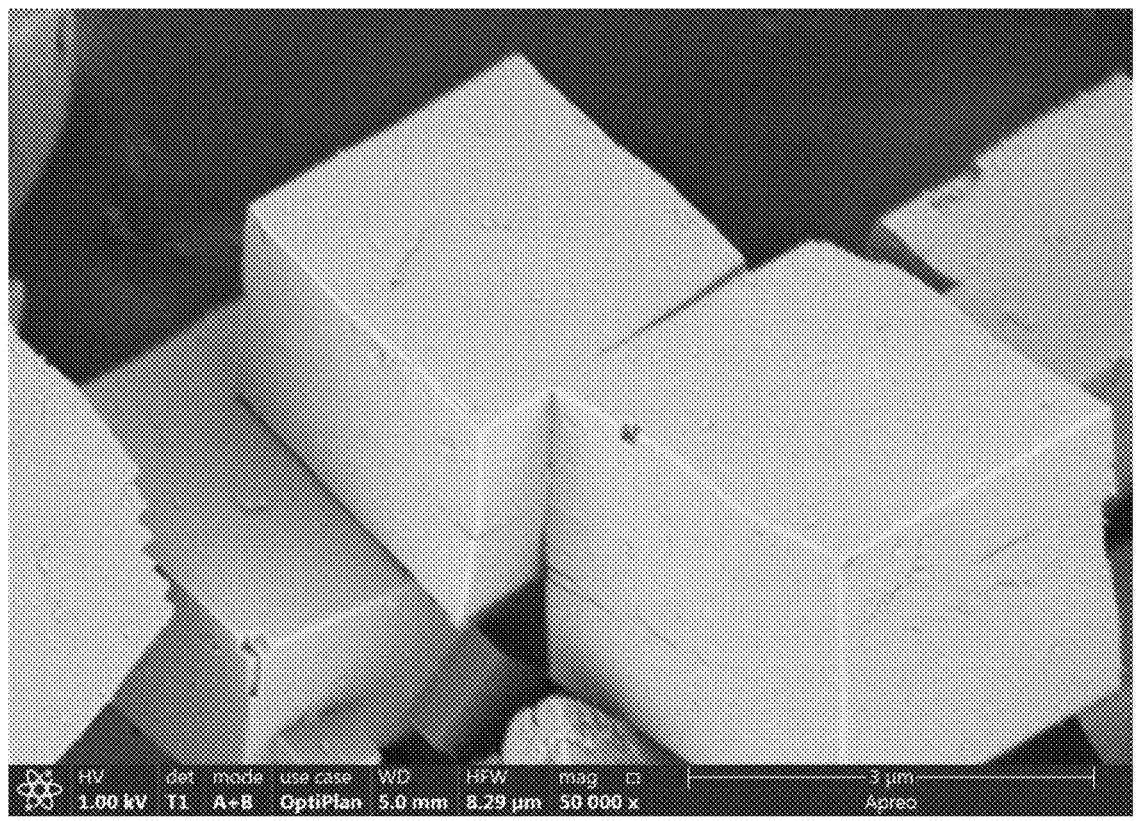
FIG. 5 is a schematic diagram showing a micro morphology of a molecular sieve product prepared in Comparative Example 1 of the present disclosure.

FIG. 5 is an SEM photo of the obtained solid product, showing that the product is cubic block-like; and XRD results indicate that the synthesized product is an SAPO-34 molecular sieve with the CHA topology.

Comparative Example 2

The addition of raw materials and the preparation process in this comparative example are the same as those in Comparative Example 1, except that two organic alkalies in a molar ratio of 1:1 are used as a mixed template. Triethylamine directs the synthesis of the CHA topology, and 2,4-dimethoxy-2,4-dimethylpentane-3-ketone (DMDMP) directs the synthesis of the AEI topology.

Figure 6:
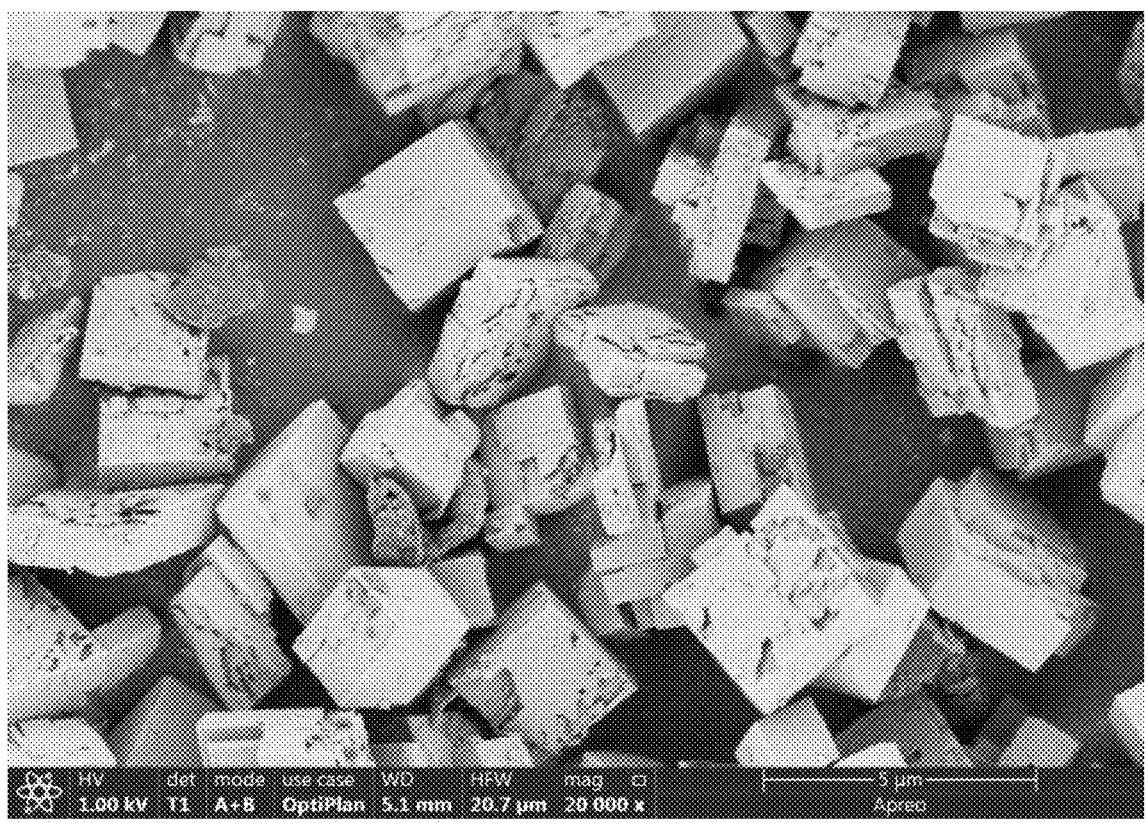
FIG. 6 is a schematic diagram showing a micro morphology of a molecular sieve product prepared in Comparative Example 2 of the present disclosure.

FIG. 6 is an SEM photo of the obtained solid product, showing that the product is cubic block-like; and XRD results indicate that the synthesized product is molecular sieves with mixed phases, including SAPO-34 or SAPO-34/SAPO-18.

Comparative Example 3

N, N, N-trimethyl-1-adamantane ammonium hydroxide is currently the mainstream template for the industrial synthesis of Na-type SSZ-13 molecular sieves with CHA topology. N, N-diethyl-2,6-dimethylpiperidine base is the mainstream template for the synthesis of SSZ-39 molecular sieves with AEI topology.

The preparation conditions, addition of raw materials, and preparation process in this comparative example are the same as those in Example 1, except that the foregoing two organic alkalies are used in a molar ratio of 1:1 as a mixed template, and the pH value is adjusted to be greater than 12 through caustic alkali.

Test results of the synthesized product show the intergrowth of SSZ-13 and SSZ-39 molecular sieves, and no molecular sieves with intergrown phases of AEI and CHA topologies is found.

Example 6

The template used in this example is shown in Formula XIII ($C_{12}H_{33}N_2O_6P$), and 20 g of the template is dissolved in 150 ml of deionized water. 2.05 g of copper nitrate is added, and a full complexing reaction is performed to form a well-mixed blue solution. The solution is stirred thoroughly at room temperature, 25 g of aluminum sol with a solid content of 30% is slowly added dropwise, and the solution is violently stirred for 30 min to form a milky blue sol-gel; 10 g of aluminum sol is added, and the sol-gel is violently stirred for 10 min; and 5 g of the remaining aluminum sol is added, and the sol-gel is violently stirred for 3 h to obtain a blue sol-gel. Subsequently, 30 g of silicon sol with a solid content of 30% is added, and the sol-gel is stirred to react for 2 h to obtain a sol-gel precursor for molecular sieve-based catalysts with intergrown phases of AEI and CHA topologies.

The precursor is stood to age for 12 h, then transferred to a hydrothermal synthesis reactor, heated to 165° C. at 4° C./min, and crystallized with stirring at a constant temperature for 24 h. After the reaction is completed, solid-liquid separation is performed by using a plate and frame filter press, a filter cake is washed repeatedly with clear water until the product is neutral, and the product is dried at 120° C. until the water content of the product is less than 6 wt %, and then calcined, and the product is heated to 350° C. at a rate of 2° C./min, preserved at a constant temperature for 1 h, then heated to 550° C., and preserved at a constant temperature for 6 h to obtain a light blue molecular sieve-based catalyst with intergrown phases of AEI and CHA topologies.

Figure 8:
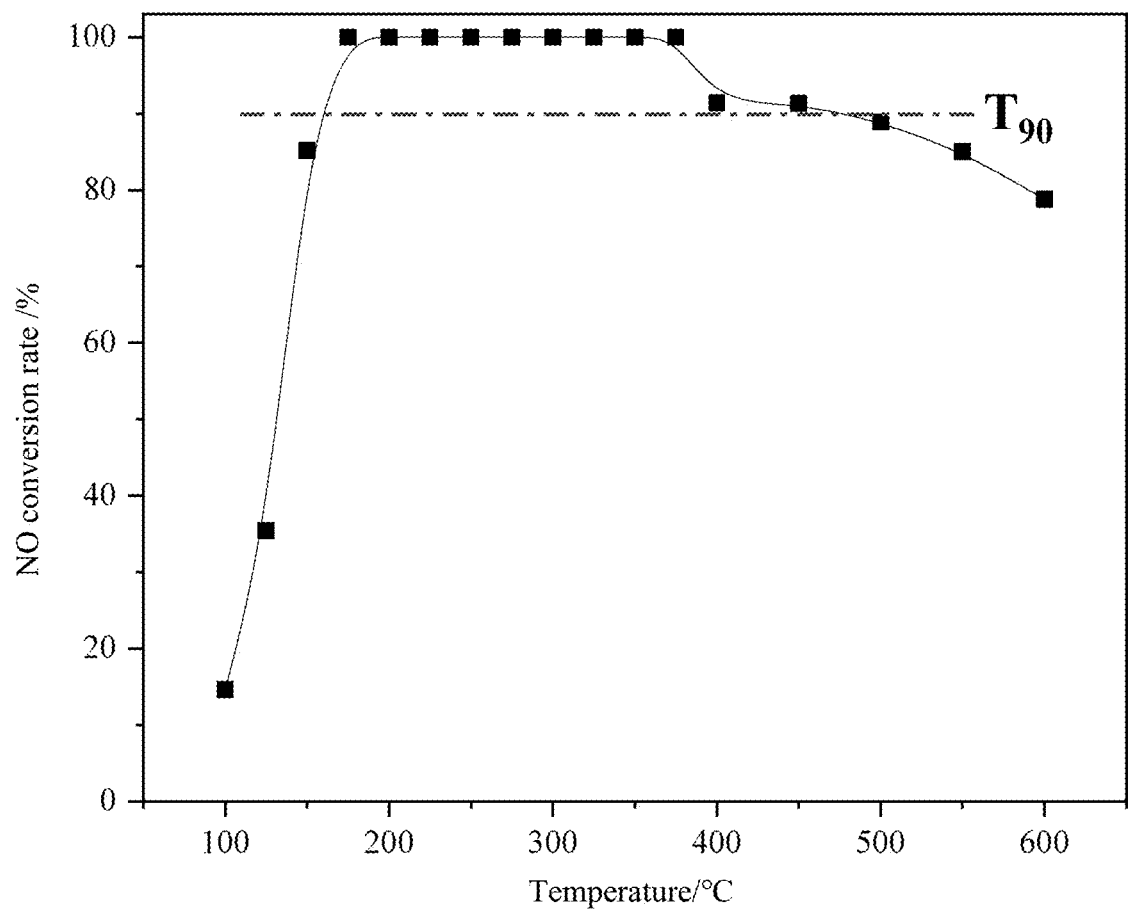
FIG. 8 is a schematic diagram showing a $NO_X$ conversion rate curve of a molecular sieve-based catalyst product prepared in Example 6 of the present disclosure.

The catalyst prepared in Example 6 is pressed into a 40-60 mesh powder sample, and $NH_3$-SCR catalytic performance is evaluated on a micro fixed bed reactor. A quartz reaction tube with a size of 15 mm is used, and a heating rate of 5° C./min is applied in the evaluation test. A simulated gas includes 500 ppm NO, 500 ppm $NH_3$, and 10% $O_2$, and $N_2$ is a balance gas, with a total flow rate of 1,000 ml/min and a reaction space velocity of 30,000 $h^{-1}$. Test results are shown in FIG. 8.

The test results show that the foregoing catalyst has a $NO_X$ ignition temperature $T_{50}$ of 130° C. and an active temperature window $T_{90}$ of 160° C.-490° C.

Example 7

The preparation conditions, addition of raw materials, and preparation process of the catalyst in this example are the same as those of the preparation of the molecular sieve-based catalyst with intergrown phases of AEI and CHA topologies in Example 1, except that the template used in this example is as shown in Formula XIV.

Example 8

On the basis of the light blue catalyst prepared in Example 6, 10 g of the catalyst is added into 100 ml of 0.2 mol/L iron nitrate solution under an ion exchange method, and a reaction occurs with stirring in a water bath at 80° C. for 8 h to prepare Cu—Fe/AEI-CHA catalysts.

Example 9

Different from Example 8, an isovolumetric impregnation method is used in this example to prepare Cu—Fe/AEI-CHA catalyst with Cu:Fe=3:1 through quantitatively controllable stoichiometry.

Example 10

Based on the preparation method of Example 9, Cu—Ce—Mn/AEI-CHA catalyst with Cu:Ce:Mn=3:1:1 are prepared.

The above descriptions are only preferred examples of the present disclosure, and are not intended to limit the present disclosure. Any modification, equivalent replacement, improvement, and the like made within the spirit and principle of the present disclosure is included in the protection scope of the present disclosure.

What is claimed is:

1. Molecular sieves with intergrown phases of AEI and CHA topologies, wherein a method for preparing the molecular sieves comprise the following steps:

(1) dissolving a hydroxyphosphono organic alkali R in water and stirring evenly; adding an aluminum source, stirring and dispersing the mixture to be gelatinous, slowly adding a silicon source, stirring and reacting for 2 h-6 h, then standing for fully aging to obtain a sol-gel precursor, wherein the aluminum source and the silicon source are calculated based on $Al_2O_3$ and $SiO_2$ respectively, a mass ratio of the silicon source, the aluminum source, the hydroxyphosphono organic alkali R, and the deionized water is $SiO_2:Al_2O_3:R:H_2O=(0.01-30):1:(0.2-30):(5-300)$, and depending on acidity and alkalinity of raw materials, a pH value of the sol-gel precursor is in a range of 6-9; and (2) putting the sol-gel precursor into a closed hydrothermal synthesis reactor for isothermal hydrothermal reaction at 130° C.-220° C. for 6.5 h-48 h, followed by pressure relief, solid-liquid separation, thorough washing of a filter cake, drying, and calcination, to obtain H-type molecular sieves with the intergrown phases of AEI and CHA topologies;

wherein the hydroxyphosphono organic alkali R has a molecular weight of less than 5,000, and contains at least one of cations shown in Formulas I-XI:

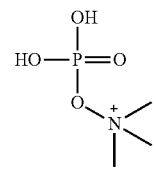

Formula I

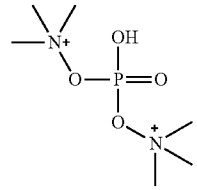

Formula II

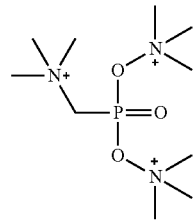

Formula III

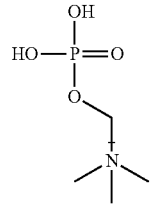

Formula IV

-continued

Formula V

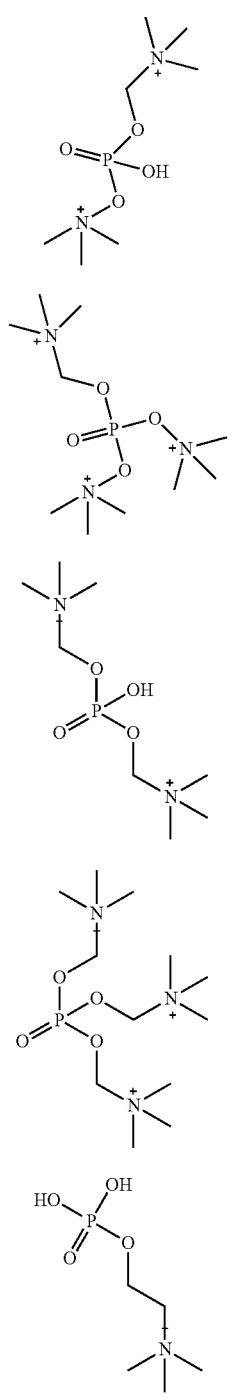

Formula VI

Formula VII

Formula VIII

Formula IX

Formula X

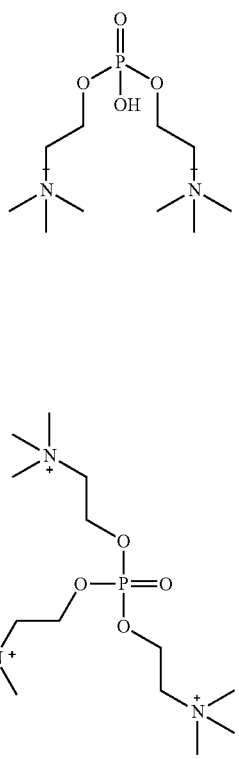

Formula XI and an anion of the hydroxyphosphono organic alkali R is at least one selected from a group consisting of $OH^-$, $NO_3^-$, $Br^-$, $HCO_3^-$, $CO_3^{2-}$, $HSO_3^-$, and $HSO_4^-$.

2. The molecular sieves according to claim 1, wherein a molecule of the hydroxyphosphono organic alkali R has a size of less than 3.7 angstroms in an aqueous phase.

3. The molecular sieves according to claim 1, wherein the molecular sieves include at least one of $AlPO_4$-18, SAPO-18, and SSZ-39 with the AEI topology and at least one of SSZ-13, SAPO-34, SAPO-44, ZK-14, and AlPO-34 with the CHA topology.

4. A catalyst, comprising the molecular sieves with the AEI and CHA symbiotic topologies according to claim 1 and an active metal element M.

5. The catalyst according to claim 4, wherein the active metal element M is at least one selected from a group consisting of Cu, Fe, Co, Mo, Mn, Sm, Pd, Pt, Rh, Au, Ag, Ru, Ni, Nb, and Cr.

* * * * *